(12) United States Patent
Demmering et al.

(10) Patent No.: US 6,683,225 B2
(45) Date of Patent: Jan. 27, 2004

(54) OXIDIC ALUMINUM/ZINC CATALYSTS AND A PROCESS OF PRODUCING UNSATURATED FATTY ALCOHOLS

(75) Inventors: Guenther Demmering, Solingen (DE); Lothar Friesenhagen, Duesseldorf (DE); Stephan Heck, Pulheim (DE); Hans Peter Kubersky, Solingen (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 354 days.

(21) Appl. No.: 09/835,657

(22) Filed: Apr. 16, 2001

(65) Prior Publication Data

US 2003/0195380 A1 Oct. 16, 2003

Related U.S. Application Data

(63) Continuation of application No. 08/653,552, filed on May 24, 1996, now abandoned.
(60) Provisional application No. 60/000,216, filed on Jun. 14, 1995.

(51) Int. Cl.$^7$ .............................. C07C 27/04; B01J 23/06
(52) U.S. Cl. ...................... 568/885; 502/340; 502/342; 502/414; 502/341; 502/343; 501/153
(58) Field of Search ................................. 502/340, 342, 502/414, 341, 343; 501/153; 568/885

(56) References Cited

U.S. PATENT DOCUMENTS

| | | | | |
|---|---|---|---|---|
| 4,565,803 A | * | 1/1986 | Schoenthal | 502/303 |
| 5,110,586 A | * | 5/1992 | Kurihara et al. | 424/76.1 |
| 5,302,569 A | * | 4/1994 | Horn et al. | 502/342 |

* cited by examiner

*Primary Examiner*—Nadine G. Norton
(74) *Attorney, Agent, or Firm*—John E. Drach

(57) ABSTRACT

Oxidic catalysts containing 20 to 25% by weight of aluminum and 40 to 50% by weight of zinc which are suitable for the production of unsaturated fatty alcohols containing 8 to 22 carbon atoms by hydrogenation of unsaturated fatty acids, fatty acid lower alkyl esters or unsaturated fatty acid glycerides are disclosed. A process for the production of the oxidic aluminum/zinc catalysts is also disclosed.

34 Claims, No Drawings

OXIDIC ALUMINUM/ZINC CATALYSTS AND A PROCESS OF PRODUCING UNSATURATED FATTY ALCOHOLS

BENEFIT OF EARLIER FILING DATE UNDER 37 CFR 1.78(A)(4)

This application is a continuation of application Ser. No. 08/653/552 filed May 24, 1996 now abandoned claims the benefit of earlier filed copending provisional application serial No. 60/000,216 filed on Jun. 14, 1995.

BACKGROUND OF THE INVENTION

1. Field of the Invention

This invention relates to oxidic aluminum/zinc catalysts, to processes for their production and to their use as catalysts for the production of unsaturated fatty alcohols.

2. Description of the Related Art

Unsaturated fatty alcohols, i.e. predominantly linear monohydric primary alcohols containing 8 to 22 carbon atoms and 1, 2 or 3 double bonds, are inter alia important raw materials for the production of cosmetic products, such as for example bath oils, make-up creams or intensive hair tonic emulsions [Seifen-Öle-Fette-Wachse, 109, 225 (1983)].

Unsaturated fatty alcohols are generally produced from native fats and oils with high iodine values, for example rapeseed oil or sunflower oil. The natural triglycerides are converted into mixtures of saturated and unsaturated fatty acid methyl esters of corresponding chain length either by pressure hydrolysis and subsequent esterification or by direct transesterification with methanol and are subsequently subjected to catalytic high-pressure hydrogenation at 200 to 350° C./250 to 300 bar. The reaction has to be controlled in such a way that only the ester group and not the double bond is hydrogenated. In practice, this high selectivity is normally achieved by using modified Adkins catalysts, for example copper-chromium or zinc-chromium spinels doped with barium or cadmium [W. Keim, Grundlagen der industriellen Chemie, Verlag Salle+Sauerländer, 1986, page 250]. To produce these spinels, copper oxide or zinc oxide is reacted with chromic acid. Since the handling of chromium(VI) compounds imposes stringent demands on work safety and waste disposal, there is a need for catalysts which, for the same selectivity, are less problematical in regard to their production and use.

Another problem is the fact that, where fats containing significant percentages of linoleic and/or linolenic acid are used, typical hydrogenation catalysts isomerize the polyunsaturated, but isolated double bonds so that increased amounts of conjugene compounds are formed in the resulting fatty alcohols and, in the same way as hydrocarbons which also accumulate as secondary products, can adversely affect the performance properties of the hydrogenation products and are therefore undesirable. Accordingly, another problem addressed by the present invention was to provide hydrogenation catalysts which would be free from these disadvantages.

SUMMARY OF THE INVENTION

The present invention relates to oxidic catalysts for the production of unsaturated fatty alcohols containing 8 to 22 carbon atoms by hydrogenation of unsaturated fatty acids, lower fatty acid alkyl esters or unsaturated fatty acid glycerides containing 20 to 25% by weight and preferably 21 to 24% by weight of aluminum and 40 to 50% by weight and preferably 45 to 49% by weight of zinc.

The invention is based on the observation that the oxidic aluminum/zinc catalysts are largely safe both in ecological and in toxicological terms. In addition, it has surprisingly been found that the catalysts according to the invention not only show high activity, they also catalyze the hydrogenation of unsaturated starting materials, for example fatty acids, fatty acid esters or triglycerides, in such a way that the double bonds in the resulting alcohols remain almost completely intact and isomerization to form conjugenes is largely suppressed. In addition, the hydrogenation products are distinguished by an advantageously low hydrocarbon content. Even after storage, the resulting unsaturated fatty alcohols are unusually light-colored and leave only a small residue after fractionation.

Another advantage of the new oxidic aluminum/zinc catalysts is that they can be used in the form of granules so that they do not have to be pelleted before hydrogenation.

Suspension Process

The present invention also relates to a process for the production of oxidic aluminum/zinc catalysts, in which a) an aluminum salt and a zinc salt in a molar ratio of 5:1 to 1:5, based on the metals zinc and aluminum, are suspended in water, b) the suspension is thoroughly mixed at elevated temperature and c) the solid formed is dried, calcined, optionally size-reduced and pelleted.

To produce the catalysts by the suspension process, the aluminum and zinc salts are suspended in water. The solids content of the resulting suspensions can be from 30 to 70% by weight and is preferably from 40 to 60% by weight, based on the suspension. In principle, the thorough mixing of the components may be carried out in any stirring machine. It has proved to be of particular advantage to carry out the thorough mixing of the components discontinuously in a kneader or continuously, for example in an extruder. The thorough mixing of the components may be carried out at elevated temperatures in the range from 50 to 100° C. and preferably in the range from 80 to 90° C.

Precipitation Process

The present invention also relates to a process for the production of oxidic aluminum/zinc catalysts in which a) a zinc salt solution is added to aqueous solutions of aluminum salts and alkali metal compounds which have a pH value of 10 to 14, b) the reaction mixture is adjusted to a pH value of 6 to 10 by addition of acids, c) the zinc aluminate precipitate formed is separated, washed, dried, calcined and mechanically size-reduced.

The aluminum and zinc salts may be used in a molar ratio of 1:5 to 5:1. In the interests of particularly high activity, long useful lives and low hydrocarbon contents in the hydrogenation products, it has proved to be of advantage to use the aluminum and zinc salts in a molar ratio of 2:1 to 1:2 and, more particularly, in a molar ratio of 1.5:1 to 1:1.5, based on the metals aluminum and zinc.

DETAILED DESCRIPTION OF THE INVENTION

To produce the catalysts by the precipitation process, an aqueous solution of an aluminum salt and an alkali metal compound, for example an alkali metal hydroxide or carbonate, is initially prepared. To obtain a clear solution, the pH value of the mixture must be in the range from 10 to 14. An aqueous solution of a zinc salt is then added in portions to the highly basic aluminate solution, a precipitate of basic zinc aluminate being formed. It does not matter whether the basic aluminate solution is initially introduced and the zinc salt solution is added thereafter or vice versa. In order quantitatively to precipitate the aluminum/zinc salt, it is advisable to carry out the precipitation with stirring at a temperature of 15 to 60° C. and to adjust the pH to a value of 6 to 10 and advantageously to a value of 7 to 8 by addition of acids, for example acetic acid or hydrochloric acid.

Starting Materials

Suitable starting materials for the production of the catalysts according to the invention are the water-soluble, optionally basic carbonates, sulfates, halides, nitrates, formates and/or acetates of aluminum and zinc. The concentration of the salts in water may be from 10 to 70% by weight and is preferably from 30 to 60% by weight, based on the solution. So far as the choice of the zinc and aluminum salts is concerned, the anions may be the same or different. Basic aluminum acetate and zinc acetate are preferably used by virtue of their high solubility in water.

Calcination

After precipitation, the precipitate is filtered off, washed and dried. To this end, the water-containing solid may be spread out in known manner, for example on trays, and dried at 100 to 180° C. to constant weight, i.e. to water contents below 1% by weight, based on the dried catalyst. For conversion into the required oxidic form, the dried catalysts are subjected to calcination, i.e. to a solid-phase reaction, at temperatures of 400 to 1,000° C. and preferably at temperatures of 500 to 950° C. Calcination may be carried out over a period of 1 to 10 hours and preferably over a period of 5 to 8 hours in a stream of hydrogen or in a stream of air. The catalysts are then mechanically size-reduced, for example by granulation.

The oxidic aluminum/zinc catalysts according to the invention are suitable in this form for the hydrogenation of unsaturated fatty acids containing 16 to 22 carbon atoms and 1, 2 or 3 double bonds, esters of these fatty acids with $C_{1-4}$ alcohols or unsaturated fatty acid glycerides, i.e. mono-, di- and/or triglycerides of aliphatic $C_{8-22}$ carboxylic acids, which have iodine values of 55 to 125 and, more particularly, 85 to 105.

Hydrogenation is normally carried out at temperatures of 200 to 350° C. and under pressures of 250 to 300 bar. The reaction parameters to be established in each individual case are primarily determined by the length of the carbon chains of the esters to be reduced. Within the limits mentioned, long-chain starting products also require high reaction temperatures. In addition, high temperatures also promote reduction of the acid value or saponification value of the hydrogenation product and hence an increase in the yield of fatty alcohols. To modify the process conditions, hydrogenation of the esters may also be carried out in the presence of lower alcohols, low-boiling paraffins or steam.

EXAMPLES

The following Examples are intended to illustrate the invention without limiting it in any way.

Example 1

1,000 g (4.5 moles) of basic zinc carbonate and 3,420 g (14.0 moles) of aluminum acetate, corresponding to a molar ratio of zinc to aluminum of 1:1.5, were introduced into a 15 liter reactor and 6 liters of deionized water were subsequently added. The suspension was heated with stirring for 6 h to 80 to 90° C. The solid formed was spread onto trays and dried for 24 h at 110° C. The catalyst was then calcined in a stream of hydrogen for 6 h at 500° C. and, following the addition of 2% by weight of flake graphite, based on the catalyst, was made up into 4×4 mm pellets in a rotary pelleting machine.

Example 2

Example 1 was repeated with 2,000 g (9.0 moles) of basic zinc carbonate and 3,420 g (14.0 moles) of aluminum acetate, corresponding to a molar ratio of zinc to aluminum of 1.3:1. Calcination was carried out in air over a period of 6 h at a temperature of 950° C.

Example 3

500 g (2.8 moles) of zinc acetate in 3.5 l of deionized water were introduced into a 7-liter three-necked flask equipped with a stirrer and dropping funnel. A mixture of 500 g (8.9 moles) of potassium hydroxide and 419 g (2.6 moles) of basic aluminum acetate in 900 ml of deionized water was added dropwise to this solution with stirring at 20° C. (pH=14), a precipitate of basic zinc aluminate being formed. In order to complete precipitation, the reaction mixture was then adjusted to a pH value of 8 by addition of 236 ml of acetic acid. The precipitate was filtered off and washed with water until no more acetate ions could be detected. The solid was then spread onto trays, dried for 12 h at 110° C. and then calcined for 12 h at 950° C. in the continuous presence of air. The calcined catalyst was then granulated to a particle size of 1 to 3 mm.

Examples 4 and 5

Hydrogenation of technical oleic acid methyl ester. 4×4 mm pellets 1,000 ml in volume of the catalyst of Example 1 were introduced into a fixed-bed reactor. Hydrogenation was carried out with technical unsaturated methyl esters (A and B) at a temperature of 300° C., under a pressure of 250 bar and at an LHSV (liquid hourly space velocity) of 0.5 $h^{-1}$. The characteristic data of the hydrogenation products are set out in Table 1.

Comparison Examples C1 and C2

Hydrogenation was carried out as in Examples 4 and 5 using a conventional chromium/zinc hydrogenation catalyst. The reaction conditions were the same as in Examples 4 and 5. The characteristic data of the hydrogenation products are set out in Table 1.

TABLE 1

| | Hydrogenation tests Percentages as % by weight | | | | | | | |
|---|---|---|---|---|---|---|---|---|
| Example # | Ester Used | Cat. | SV | OHV | IV | CC % | US % | Color |
| 3 | A | Al/Zn | 0.7 | 203 | 109 | 2.2 | 1.3 | Colorless |
| 4 | B | Al/Zn | 1.0 | 205 | 92 | 1.0 | 1.2 | Colorless |
| C1 | A | Cr/Zn | 1.7 | 203 | 92 | 11.0 | 2.0 | Yellow |
| C2 | B | Cr/Zn | 1.7 | 206 | 92 | 7.6 | 2.0 | Yellow |

Legend:

E.   = Ester
Cat. = Catalyst
AV   = Acid value
SV   = Saponification value
OHV  = Hydroxyl value
IV   = Iodine value
CC   = Conjugene content
US   = Unsulfonatable components (mainly hydrocarbons)
A    = Methyl ester based on rapeseed oil, non-hydrogenated EDENOR ® MERa, SV = 175, IV = 97
B    = Methyl ester based on animal oleic acid EDENOR ® MeTiO5, SV = 195, IV = 90 both commercial products of Henkel KGaA, Duesseldorf/FRG

What is claimed is:

1. A calcined oxidic aluminum/zinc catalyst consisting essentially of:

(a) from about 20 to about 25% by weight of aluminum and (b) from about 40 to about 50% by weight of zinc; wherein aluminum and zinc are the only metal components of the catalyst.

2. A process for the production of a calcined oxidic aluminum/zinc catalyst of claim 1 comprising the steps of:
(a) suspending, in water, a zinc compound selected from the group consisting of water-soluble carbonates, sulfates, halides, nitrates, formates, acetates, and combinations thereof and an aluminum compound selected from the group consisting of water-soluble carbonates, sulfates, halides, nitrates, formates, acetates, and combinations thereof,
(b) mixing thoroughly the suspension formed in step (a) at a temperature of from about 50 to about 100° C. to form an aluminum/zinc solid,
(c) drying and calcining the product formed in step (b), wherein the molar ratio of aluminum to zinc is from about 5:1 to about 1:5 and the solids content of the suspension formed in step (a) is from about 30 to about 70% by weight of the suspension; and wherein aluminum and zinc are the only metal components of the catalyst.

3. The process of claim 2 wherein basic aluminum and basic zinc compounds selected from the group consisting of water-soluble carbonates, sulfates, halides, nitrates, formates, acetates, and combinations thereof are used in step (a).

4. The process of claim 2 wherein the solids content of the suspension formed in step (a) is from about 40 to about 60% by weight of the suspension.

5. The process of claim 2 wherein step (b) is carried out at a temperature of from about 80 to about 90° C.

6. The process of claim 2 wherein the product formed in step (b) is dried at a temperature of from about 100 to about 180° C. and to a water content below 1%.

7. The process of claim 2 wherein the dried product of step (c) is calcined at a temperature of from about 400 to about 1000° C.

8. The process of claim 2 wherein the dried product of step (c) is calcined for a time period of from about 1 to about 10 hours.

9. The process of claim 2 wherein the dried, calcined product of step (c) is modified by mechanically size reducing, mixing with from about 0.5 to about 5% graphite by weight of said product, as a lubricant, and pelleting.

10. A process for the production of a calcined oxidic aluminum/zinc catalyst of claim 1 comprising the steps of:
(a) combining an aqueous solution of a zinc compound selected from the group consisting of water-soluble carbonates, sulfates, halides, nitrates, formates, acetates, and combinations thereof with an aqueous solution of an aluminum compound selected from the group consisting of water soluble carbonates, sulfates, halides, nitrates, formates, acetates, and combinations thereof in addition to an aqueous alkali metal solution having a pH of from about 10 to about 14,
(b) mixing the aqueous solution produced in step (a), to produce a basic zinc aluminate precipitate,
(c) adding an acid to the solution of step (b) producing a solution having a pH of from about 6 to about 10, to quantitatively precipitate the basic zinc aluminate solid of step (b),
(d) separating, washing, drying, calcining and mechanically size reducing the basic zinc aluminate precipitate formed in step (c) to form said oxidic aluminum/zinc catalyst, wherein the molar ratio of aluminum to zinc is from about 5:1 to about 1:5; and wherein aluminum and zinc are the only metal components of the catalyst.

11. The process of claim 10 wherein the molar ratio of aluminum to zinc is from about 2:1 to about 1:2.

12. The process of claim 11 wherein said molar ratio is from about 1.5:1 to about 1:1.5.

13. The process of claim 10 wherein basic aluminum and basic zinc compounds selected from the group consisting of water-soluble carbonates, sulfates, halides, nitrates, formates, acetates, and combinations thereof are used in step (a).

14. The process of claim 10 wherein the precipitate in step (d) is dried at a temperature of from about 100 to about 180° C. and to a water content below 1%.

15. The process of claim 10 wherein the dried, calcined catalyst of step (d) is modified by mixing with from about 0.5 to about 5% graphite by weight of said catalyst, as a lubricant, and pelleting.

16. The catalyst of claim 1 wherein the oxidic catalyst consists essentially of from about 21 to about 24% by weight of aluminum and from about 45 to about 49% by weight of zinc.

17. The process of claim 3 wherein said solids content of the suspension formed in step (a) is from about 40 to about 60% by weight.

18. The process of claim 4 wherein step (b) is carried out at a temperature in the range of from about 80 to about 90° C.

19. The catalyst prepared by the process of claim 2.

20. The catalyst prepared by the process of claim 10.

21. The catalyst of claim 1 wherein the catalyst had been calcined for a period of from about 1 to about 10 hours at a temperature in the range of from about 500 to about 1,000° C.

22. The catalyst of wherein the catalyst had been calcined at a temperature the range of from about 500 to about 950° C.

23. The process of claim 10 wherein step (c) is carried out at a temperature in the range of from about 15 to about 60° C.

24. The process of claim 10 wherein in step (c) the pH is from about 7 to about 8.

25. A process for the production of a calcined oxidic aluminum/zinc catalyst consisting essentially of
(i) from about 20 to about 25% by weight of aluminum, and
(ii) from about 40 to about 50% by weight of zinc; wherein aluminum and zinc are the only metal components of the catalyst, comprising the steps of:
(a) combining an aqueous solution of a zinc compound selected from the group consisting of water-soluble carbonates, sulfates, halides, nitrates, formates, acetates, and combinations thereof with an aqueous solution of an aluminum compound selected from the group consisting of water-soluble carbonates, sulfates, halides, nitrates, formates, acetates, and combinations thereof in addition to an aqueous alkali metal solution having a pH of from about 10 to about 14,
(b) mixing the aqueous solution produced in step (a), to produce a basic zinc aluminate precipitate,
(c) adding an acid to the solution of step (b) producing a solution having a pH of from about 6 to about 10, to quantitatively precipitate the basic zinc aluminate solid of step (b),
(d) separating, washing, drying, calcining at a temperature of from about 500 to about 1000° C, and mechanically size reducing the basic zinc aluminate precipitate formed in step (c) to form said oxidic aluminum/zinc catalyst, wherein the molar ratio of aluminum to zinc is from about 5:1 to about 1:5.

26. The process of claim 25 wherein the dried precipitate of step (d) is calcined for a time period of from about 1 to about 10 hours.

27. A process for the production of a calcined oxidic aluminum/zinc catalyst comprising the steps of
   a) suspending a water-soluble zinc compound, and a water-soluble aluminum compound in water;
   b) thoroughly mixing the suspension formed in step a) at an elevated temperature to form an aluminum/zinc solid; and
   c) drying and calcining the aluminum/zinc solid formed in step b); wherein aluminum and zinc are the only metal components of the catalyst.

28. The catalyst prepared by the process of claim 27.

29. A process for the production of a calcined oxidic aluminum/zinc catalyst comprising the steps of:
   I) combining an aqueous solution of a water-soluble zinc compound with an aqueous solution of a water-soluble aluminum compound and an aqueous alkali metal solution;
   II) mixing the aqueous solution produced in step I to produce a basic zinc aluminate precipitate;
   III) adding an acid to the solution of step II to quantitatively precipitate the basic zinc aluminate solid of step II;
   IV) separating, washing, drying, calcining and mechanically size reducing the basic zinc aluminate precipitate formed in step III to form said oxidic aluminum/zinc catalyst;

wherein aluminum and zinc are the only metal components of the catalyst.

30. A method of producing unsaturated fatty alcohols comprising contacting an unsaturated fatty acid lower alkyl ester or deacidified unsaturated fatty acid glyceride with hydrogen in the presence of the catalyst prepared by the process of claim 1.

31. A method of producing unsaturated fatty alcohols comprising contacting an unsaturated fatty acid lower alkyl ester or deacidified fatty acid glyceride with hydrogen in the presence of the catalyst of claim 1.

32. A method of producing unsaturated fatty alcohols containing 8 to 22 carbon atoms comprising contacting an unsaturated fatty acid lower alkyl ester or deacidified unsaturated fatty acid glyceride with hydrogen in the presence of the catalyst of claim 1.

33. The method of claim 32 wherein the reaction is carried out at a pressure of from about 250 to about 300 bars.

34. The method of claim 32 wherein the reaction is carried out at a temperature of from about 200 to 350° C.

* * * * *